(12) United States Patent
Painchaud et al.

(10) Patent No.: US 8,894,617 B2
(45) Date of Patent: Nov. 25, 2014

(54) SAFETY DEVICE FOR AN INJECTION DEVICE

(75) Inventors: Gaetan Painchaud, Francheville (FR); Pascal Dugand, Estrablin (FR); Xavier Julia, Villefontaine (FR)

(73) Assignee: Rexam Healthcare la Verpilliere (FR)

( * ) Notice: Subject to any disclaimer, the term of this patent is extended or adjusted under 35 U.S.C. 154(b) by 1020 days.

(21) Appl. No.: 12/480,424

(22) Filed: Jun. 8, 2009

(65) Prior Publication Data

US 2010/0016805 A1    Jan. 21, 2010

(30) Foreign Application Priority Data

Jun. 6, 2008 (FR) ...................................... 08 53767

(51) Int. Cl.
*A61M 5/32* (2006.01)
*A61M 37/00* (2006.01)

(52) U.S. Cl.
CPC ....... *A61M 5/326* (2013.01); *A61M 2005/3264* (2013.01); *A61M 37/00* (2013.01)
USPC ............................ 604/198; 604/192; 604/263

(58) Field of Classification Search
CPC ...................................................... A61M 5/32
USPC ........................... 604/192, 198, 263, 218, 283
See application file for complete search history.

(56) References Cited

U.S. PATENT DOCUMENTS

| | | | | | |
|---|---|---|---|---|---|
| 4,767,413 | A | * | 8/1988 | Haber et al. ................... | 604/198 |
| 4,795,432 | A | * | 1/1989 | Karczmer ...................... | 604/110 |
| 5,295,963 | A | * | 3/1994 | Deeks ............................ | 604/110 |
| 6,319,233 | B1 | * | 11/2001 | Jansen et al. .................. | 604/192 |
| 7,297,136 | B2 | * | 11/2007 | Wyrick .......................... | 604/117 |
| 2005/0159706 | A1 | | 7/2005 | Wilkinson et al. | |

FOREIGN PATENT DOCUMENTS

| | | |
|---|---|---|
| DE | 10359694 A1 | 7/2005 |
| FR | 2778853 A1 | 11/1999 |
| FR | 2830765 A1 | 4/2003 |
| WO | 2007138299 A1 | 12/2007 |

OTHER PUBLICATIONS

French Search Report & Written Opinion; FR 0853767; Feb. 13, 2009; 6 pages.

* cited by examiner

*Primary Examiner* — Edelmira Bosques
(74) *Attorney, Agent, or Firm* — St. Onge Steward Johnston & Reens LLC

(57) ABSTRACT

A safety device for an injection device including a protective sheath driven by a spring, the safety device being capable of taking an injection configuration in which the sheath allows an injection needle to be left uncovered, and a safe configuration in which the sheath enables the injection needle to be covered; retractable catches for retaining the spring, the retractable catches retaining the spring under stress in such a manner as to hold the safety device in the injection configuration; and deactivation mechanism for deactivating the retractable catches, enabling the safety device to take a storage configuration in which the retractable catches are not subjected to stress from the spring.

11 Claims, 4 Drawing Sheets

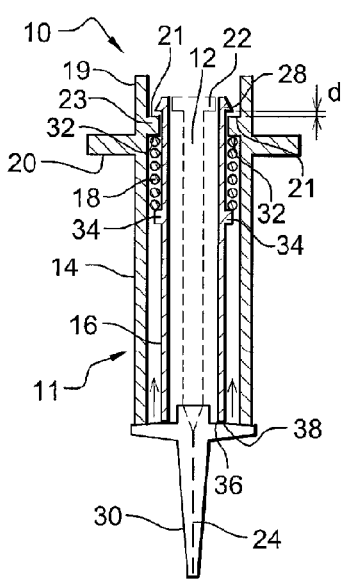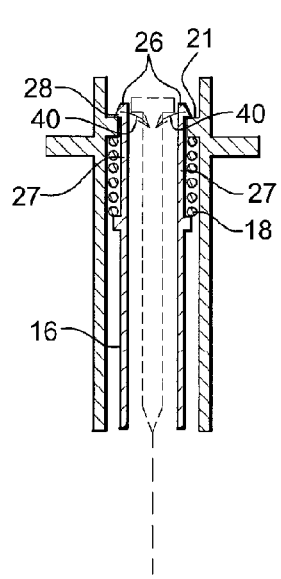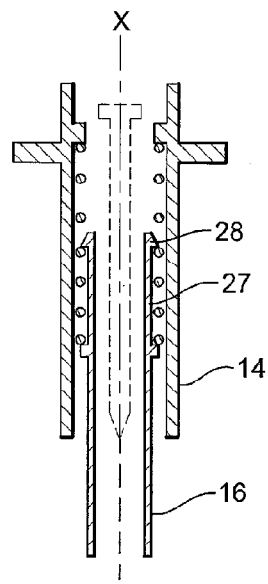
Fig. 1  Fig. 2  Fig. 3
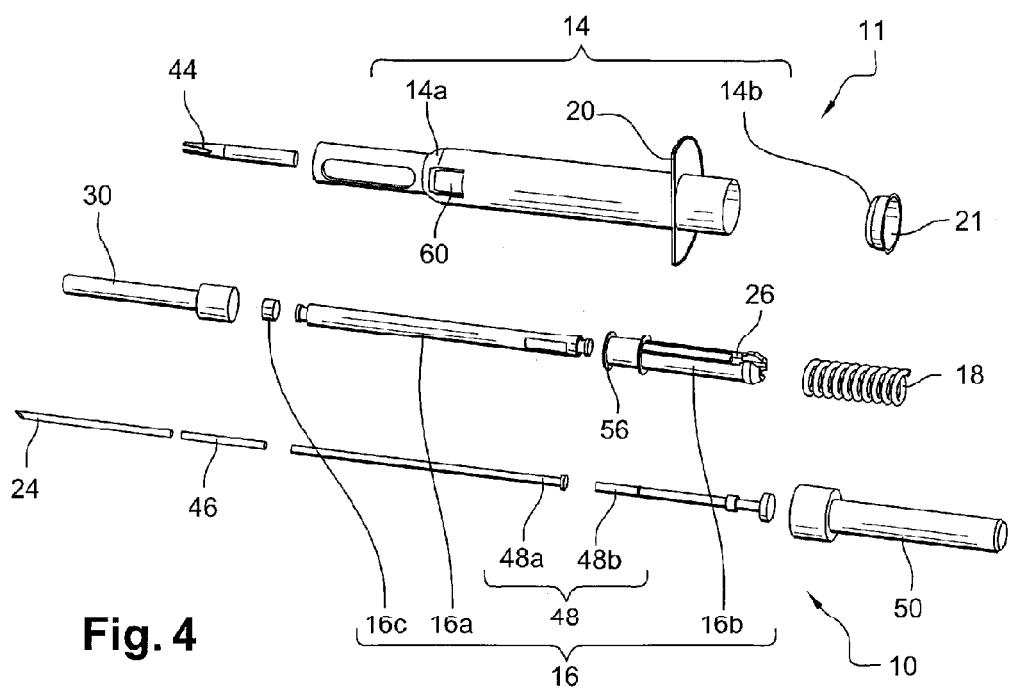
Fig. 4

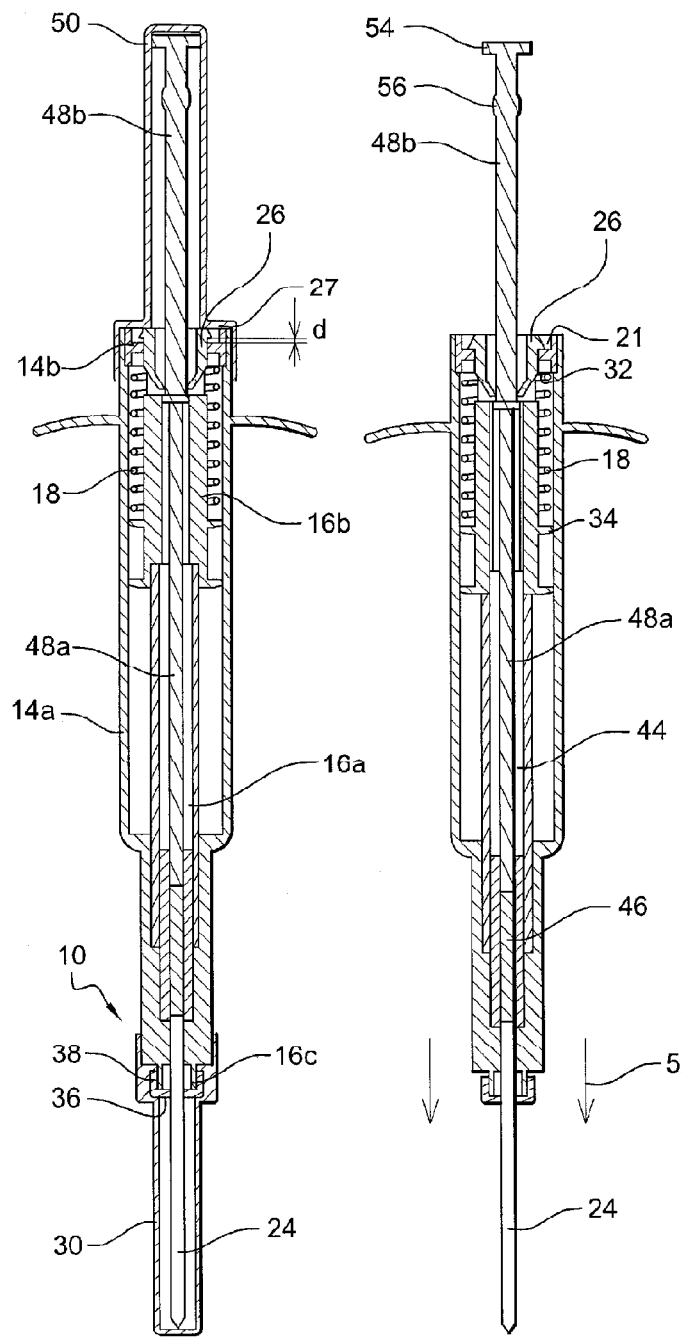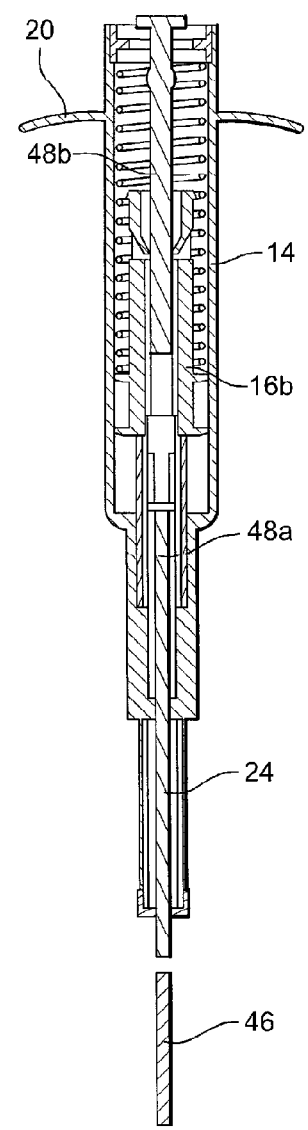
Fig. 5          Fig. 6          Fig. 7

SAFETY DEVICE FOR AN INJECTION DEVICE

CROSS-REFERENCE TO RELATED APPLICATIONS

The present application claims priority of French patent application No. 0853767 filed on Jun. 6, 2008.

FIELD OF THE INVENTION

The present invention relates to the field of safety devices for injection devices. More precisely, but not exclusively, such safety devices are incorporated in devices for injecting a substance into the body of a subject, which substance may be in the form of a liquid contained in an injection syringe, or it may be in the form of an implant, i.e. a compound in the solid or semi-solid state and injected in intramuscular or subcutaneous manner.

BACKGROUND OF THE INVENTION

A safety device for an injection device is already known, such as that described in document FR 2 830 765. that is provided with a syringe carrying a needle and a sheath for protecting the needle. The sheath may occupy an injection position, leaving the needle uncovered, or a safe position, in which it covers the needle. The sheath is driven by a spring that is compressed while the sheath is in the injection position and that is expanded while the sheath is in the safe position. In order to control the movement of the spring, the safety device is provided with retractable tabs holding the spring in the compressed position during injection.

Prior to being used, the safety device is generally stored in its injection position, and thus in a position in which the spring is under stress.

It is found that the retractable tabs retaining the spring can become damaged by wear while the device is in storage, particularly since storage may last for several years. More precisely, the retractable tabs are often made of a flexible plastics material and can suffer a certain amount of creep over time, particularly since they are subjected to tension from the compressed spring applying a certain amount of stress thereto. As a result, the safety device might become faulty if it is not used within a certain length of time.

A particular object of the invention is to resolve that drawback by proposing a safety device that is guaranteed to operate properly even after being stored for a relatively long time prior to use.

SUMMARY OF THE INVENTION

To this end, the invention provides a safety device for an injection device, the safety device comprising:
 a protective sheath driven by return means, the safety device being capable of taking an injection configuration in which the sheath allows an injection needle to be left uncovered, and a safe configuration in which the sheath enables the injection needle to be covered;
 retractable means for retaining the return means, the retractable means retaining the return means under stress in such a manner as to hold the safety device in the injection configuration; and
 deactivation means for deactivating the retractable means, enabling the safety device to take a storage configuration in which the retractable means are not subjected to stress from the return means.

It is thus proposed to spare the retractable means during storage of the safety device, by avoiding them being put under tension, i.e. by avoiding them being subjected to the stress that is exerted thereon by the return means when the safety device is in the injection configuration.

Preferably, while in the storage configuration, the means for deactivating the retractable means exert stress on the return means that is greater than the stress exerted by the retractable means in the injection configuration, so that the retractable means are not subjected to stress during storage.

For example, the return means may be a spring in compression, occupying a compressed position, i.e. a stressed position, in the injection configuration of the device, and an extended position in the safe configuration, thereby pushing the sheath so that it covers the needle. In this example, the means for deactivating the retractable means exert compression on the spring that is greater than the compression that is exerted thereon in the injection configuration. Thus, since the spring is more compressed in the storage configuration, it no longer "pulls" on the retractable means.

By avoiding putting the retractable means under tension while they are in storage, the risk of the material from which they are made creeping is considerably reduced, thereby reducing the risk of the safety device failing.

It will be understood that the means for deactivating the retractable means act advantageously in such a manner that the deactivated retractable means, when in the storage configuration, no longer exert their function of retaining the return means. It should also be observed that the above-mentioned three configurations of the safety device (injection, safe, and storage configurations) correspond to configurations that are distinct from one another.

Amongst the other advantages of the safety device, it should be observed that because the retractable means are spared, there is no need for these retractable means to be as robust as when they are under stress during storage, thus making it possible to provide retractable means of a different shape, and in particular of reduced size and thickness. In addition, it is possible for them to be made of a material that withstands creep less well than the materials used at present, and in particular a material that is less expensive. Furthermore, by this storage during which the retractable means are deactivated, any risk of the safety device triggering accidentally during storage is reduced. This is particularly advantageous, firstly during transport since vibration and impacts can accidentally trigger the device, and secondly during sterilization operations since they can cause the retractable means to suffer creep that degrades their operation, and might even cause them to retract accidentally. Finally, the safety device proposed avoids any need to verify that the device has not been damaged before it is used.

The safety device may also include one or more of the following characteristics.

The retractable means for retaining the return means comprise retractable catches, the catches being in abutment against a surface when the device is in the injection configuration and being retracted from said abutment when the device is in the safe configuration; the deactivation means holding the catches at a certain distance from the abutment when the device is in the storage configuration. Thus, deactivation of the retractable means amounts to disengaging them from the abutment through which they act to retain the return means.

The deactivation means comprise a protective cap covering the needle when the device is in the storage configuration, fitting the cap on the safety device causing the retractable means to be deactivated, preferably by moving the protective sheath. Thus, fitting the cap on the injection device enables it to be put automatically into its storage configuration. Subsequently removing the cap, immediately before injection, automatically stops the action of the deactivation means, such that the retractable means are activated and the injection device takes on its injection configuration. For example, the cap may be screwed onto the injection device and the sheath may carry the retractable means; screwing on the cap moves the sheath a little together with the retractable means, preferably moving the retractable means away from the abutment with which they are designed to co-operate. The use of such a cap is particularly effective since it avoids any need to provide an additional part carrying the deactivation means, given that the cap serves both to protect the needle in the storage configuration and to deactivate the retractable means.

The deactivation means comprise a storage member mounted on the proximal end of the safety device and bearing directly or indirectly against the return means to cause them to take up their storage configuration. Thus, a part is fitted onto the proximal end of the device, and that can lead to several advantages. This part can protect or lock the device during storage, by preventing or limiting movement of the piston rod. In addition, this part may cover the proximal end of the device so as to block access to the substance contained therein. For example, the part may prevent an ill-intentioned person from taking substance by passing a needle along the inside of the piston from the proximal end in order to draw off the substance.

The member comprises removable fastener means on the safety device and a distal portion extending from the fastener means and forming a spacer between the fastener means and the return means. This distal portion of the member may form a spacer either bearing directly (with contact) against the return means, or bearing indirectly, e.g. by pressing against the collar of a syringe on which the return means act. By means of this spacer-forming portion, it is possible to hold the return means at a certain distance from the retractable means, in order to avoid stressing them during storage.

The storage member includes means for protecting a piston rod. These protection means may include a housing for receiving the piston rod, which housing may be opened or closed, e.g. semi-tubular, and configured in such a manner as to prevent bending, breaking, or even accidental or deliberate movement of the piston rod during storage. In other words, the reception housing forms a protective case for the piston rod, limiting access thereto. Thus, the storage member performs two functions: firstly it spares the retractable means, and secondly it protects the piston rod.

The injection device is a device for injecting an implant in the solid or semi-solid state, preferably a device for retro-injection of the implant. A retro-injection device provides technical features that are associated with a certain amount of mechanical complexity, so it is particularly advantageous to use a solution that is simple as described above in order to guarantee that the device operates properly. A device for retro-injection of an implant presents in particular means for injecting the implant into the patient's body while the needle is being withdrawn therefrom. The advantage of implant retro-injection is to avoid exerting stress on the implant at the moment it leaves the needle so as to remain in the patient's body, unlike a simple injection where the substance is pushed or compressed into the patient's skin. During retro-injection, the implant fills an empty space left by the needle as it is withdrawn. Thus, the implant injection device often requires special means for retaining the implant prior to injection and also for keeping the implant in position in the patient's skin while the needle is being withdrawn.

The injection device is a liquid injection device comprising a syringe for injecting a liquid or a gel. The syringe may optionally be a standard glass syringe having no special means for providing safety, such means forming part of the safety device. In addition to the sheath, the safety device may include an intermediate part in which the syringe is snap-fastened, at least while the device is in the safe configuration. Alternatively, the syringe may be made of plastics material, and need not necessarily be of standard shape.

The invention also provides an injection device including a safety device as described above.

As mentioned above, the injection device may optionally be a device for injecting an implant, including means for retro-injection of the implant, or it may be a device for injecting a liquid, including a liquid injection syringe.

The invention also provides a method of assembling the injection device, the sheath being slidably mounted relative to an intermediate body, and the return means being retained firstly against the sheath and secondly against the intermediate body, in which method a piston rod or a syringe is fitted to the injection device once the safety device is in the storage configuration. During such assembly, the deactivation means perform two functions, firstly they avoid the retractable means being damaged during storage, and secondly they avoid unwanted retraction of the retractable means while the injection device is being assembled, more precisely at the moment the piston or the syringe is being assembled on the safety device.

BRIEF DESCRIPTION OF THE DRAWINGS

The invention can be better understood on reading the following description given purely by way of example and made with reference to the drawings, in which:

FIG. 1 is a diagrammatic longitudinal section view of an embodiment of a safety device in a storage configuration;

FIG. 2 is a view similar to FIG. 1, the safety device being in an injection configuration;

FIG. 3 is a view similar to FIG. 1, the safety device being in a safe configuration;

FIG. 4 is an exploded view of an implant injection device in another embodiment;

FIG. 5 is a longitudinal section view of the FIG. 4 device in a storage configuration;

FIG. 6 is a view similar to FIG. 5, the injection device being in an injection configuration;

FIG. 7 is a view similar to FIG. 5, the injection device being in a safe configuration;

DETAILED DESCRIPTION OF THE INVENTION

Figure 8:
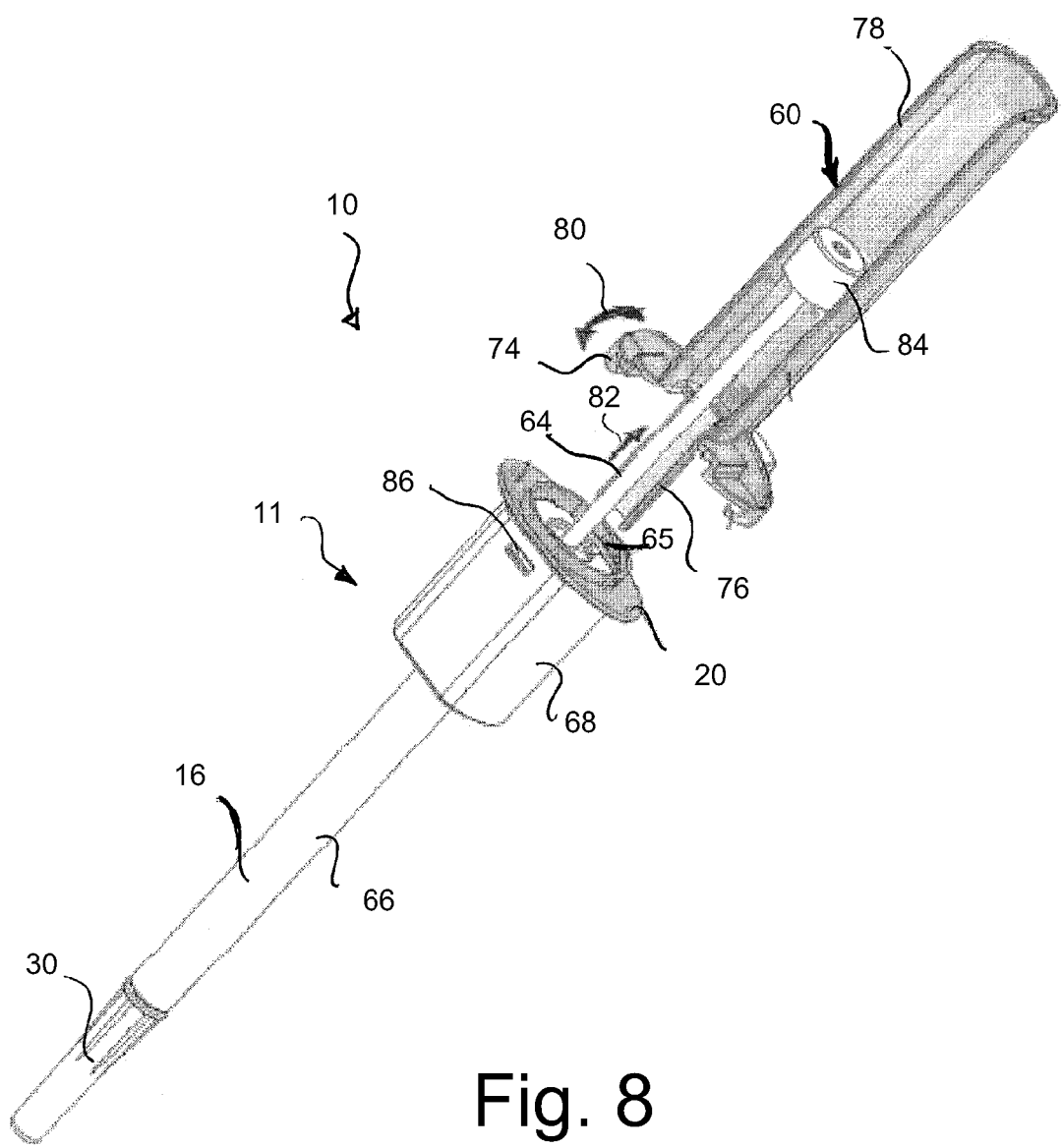
FIG. 8 is a perspective view of a liquid injection device in yet another embodiment.

FIGS. 1 to 3 show an injection device 10 comprising an embodiment of a safety device 11 together with an injection syringe 12.

It should be observed that these FIGS. 1 to 3 are highly diagrammatic for the purpose of illustrating the operation proposed by the invention, and they do not show all of the functions of the injection device 10.

As described below, the safety device 11 can take at least three distinct configurations, namely a storage configuration shown in FIG. 1, an injection configuration shown in FIG. 2, and a safe configuration shown in FIG. 3.

The safety device comprises an intermediate body 14 and a protective sheath 16 mounted to slide inside the intermediate body 14, the sheath 16 being driven by return means 18. In this example the return means are constituted by a spring in compression 18.

In this element, the intermediate body 14 is cylindrical and carries means 20 for gripping the device, specifically finger grips 20 deigned to be held by the user while making an injection. Furthermore, the intermediate body 14 includes an abutment surface 21 at its proximal end 19, the abutment surface being carried in this example by two projections 23. Still in this example, the protective sheath 16 is cylindrical and is slidably mounted inside the intermediate body 14.

The syringe 12 shown in dashed lines is provided with a piston (not shown). In this example, the syringe 12 is permanently secured to the intermediate body 14 regardless of the configuration of the safety device 11. More precisely, the syringe 12 includes a collar 22 snap-fastened in the intermediate body 14, by means that are not shown. Furthermore, at its distal end, the syringe 12 carries an injection needle 24.

The protective sheath 16 can take at least three distinct positions in the safety device 11, namely a storage position, an injection position, and a safe position, corresponding to the positions taken by the sheath 16 in the storage, injection, and safe configurations respectively of the injection device shown in FIGS. 1, 2, and 3. In the injection position shown in FIG. 2, the protective sheath 16 enables the injection needle 24 to be left uncovered, so that it can penetrate into the skin of a patient. In the safe position shown in FIG. 3, the protective sheath 16 serves to cover the injection needle 24, in particular to prevent any risk of contamination once an injection has been made.

As can be seen in FIG. 2, the protective sheath 16 includes retaining means 26 for retaining the return means 18. These retaining means 26 are retractable. They can take a deactivated position in the storage configuration of the device, a retaining position in the injection configuration, and a retracted position in the safe configuration of the device 11. In this example, the retaining means 26 comprise two diametrically-opposite resilient tabs 27 extending in the longitudinal direction X of the device, with the proximal ends of the tabs 27 carrying retractable catches 28, being movable elastically in a radial direction.

Like the protective sheath 16, the return means 18 can take up storage, injection, and safe positions corresponding to the positions taken by the return means 18 when the device 11 is respectively in its storage, injection, and safe configurations. For this purpose, as means for retaining the return means 18, in addition to the retractable means 26, the device 11 includes a proximal abutment surface 32 carried in this example by the projections 23 of the intermediate body 14, and a distal abutment surface 34 carried by two projections formed on the protective sheath 16. Thus, the proximal end of the return means 18 is in abutment against the surface 32 and the distal end thereof is in abutment against the surface 34.

The safety device 11 also has a protective cap 30, covering the needle 24 when the device 11 is in the storage configuration, e.g. mounted on the intermediate body 14 by screw fastening. In this example, when the cap 30 is screwed onto the device 11, the device is in its storage configuration, as described below.

In this example, the cap 30 includes means for deactivating the retractable means 26. Because of these deactivation means, the safety device 11 can take on the storage configuration of FIG. 1 in which the retractable means 26 are not subjected to stress by the return means 18, as can be understood from the way the device operates, as described below.

In the storage configuration shown in FIG. 1, the cap 30 is mounted on the intermediate body 14 by screw fastening, this screw fastening causing the protective sheath 16 to be moved a little, as represented by arrows in FIG. 1. More precisely, the cap 30 carries an abutment surface 36 that moves in the direction X while the cap 30 is being screwed on, thereby moving the distal end 38 of the protective sheath 16. As a result of this movement of the protective sheath 16, the retractable means 26 also move through a distance d and they are no longer in contact with the abutment surface 21. Thus, the deactivation means 30 hold the catches 28 at a distance d (shown in FIG. 1) from the abutment 21 while the device is in its storage configuration. Because of this movement, the retaining means 26 are not subjected to stress by the return means 18, i.e. the return means 18 do not exert their return force on the catches 28. The compressed return means 18 exert their return force, not on the retractable means 26, but rather on the abutments 32 and 34, and thus on the cap 30 which receives the thrust from the protective sheath 16 against the abutment 36.

As explained above, in this storage configuration, the safety device 11 (with or without the syringe 12) can be stored prior to use without any risk of damaging the retractable means 26.

The injection configuration of the device 11 is shown in FIG. 2. In this configuration, the needle 24 is left uncovered, and can therefore be pushed into the skin of a patient in order to inject the substance. To go from the storage configuration to the injection configuration, the user removes the cap 30 by unscrewing it from the intermediate body 14. With the cap removed, the protective sheath 16 is no longer held by the abutment 36, so the return means 18 exert their force on the abutment 34 and move the sheath downwards through a distance close to the distance d, until the catches 28 come into contact with the abutment 21. As can be seen in FIG. 2, the retractable means 26 retain the return means 18 in the injection position, a position in which the protective sheath 16 leaves the needle uncovered and in which the retractable means 26 are in contact with the abutment 21. In this configuration, the substance can be injected into the body of the patient.

Once the substance has been injected, the device takes on its safe configuration as follows. When the piston reaches the end of its stroke, the retractable means 26 are retracted from the abutment 21, e.g. by being pushed inwards by the proximal end of the piston rod, as shown by arrows 40 in FIG. 2, such that the retraced means 26 no longer perform their function of retaining the return means 18. As a consequence, the protective sheath 16 is urged forwards by the expanding return means 18, thereby covering the needle 24. In this configuration, the safety device 11 protects the needle so as to prevent contamination after injection. It should be observed that the stroke of the protective sheath 16 is preferably limited by abutments provided on the intermediate body 14 and the protective sheath 16, which abutments are not shown.

FIGS. 1 to 3 are shown with a syringe 12 suitable for injecting a substance in liquid form, however the safety device 11 can also be used with a device for injecting an implant in a solid or semi-solid state, and having means other than a syringe for injecting a liquid.

Furthermore, it should be observed that a particularly advantageous aspect of the way the injection device 10 is assembled lies in the fact that it is possible to fit the prefilled syringe 12 together with its piston, once the safety device 11 is in its storage configuration. This embodiment is advantageous because it is possible to store the safety device 11 independently of the liquid-containing syringe. By means of the above-described device, when the syringe 12 together with its piston is fitted thereto, e.g. by snap-fastening the collar 22 in the body 14, no stress is applied to the retractable means 26, since these means 26 are not subjected to stress from the return means 18 while in the storage configuration. In other words, since the return means 18 do not exert any force on the retractable means 26, but rather on the cap 30, there is no danger that inserting the syringe 12, which might cause the device 11 to be jolted, will accidentally trigger retraction of the means 26, as would happen if the syringe 12 were to be inserted while the safety device 11 was in its injection configuration, as shown in FIG. 2.

It will be understood that in the storage configuration, the deactivation means 30 exert stress on the return means 18 that is greater than the stress exerted by the retractable means 26 while in the injection configuration.

FIGS. 4 to 7 show an example of a device for injecting an implant. In this device, elements having functions similar to those of the embodiment of FIGS. 1 to 3 are specified by identical references.

The safety device 11 comprises an intermediate body 14, a protective sheath 16, return means 18, and a protective cap 30. In addition to the safety device 11, the injection device 10 includes a member 44 for receiving an implant 46, an injection needle 24 and a piston rod 48. The rod 48 has a distal portion 48a and a proximal portion 48b that is spaced apart from the distal portion 48a. The distal portion is not necessarily separate from the proximal portion. Finally, the device 10 includes means 50 for preventing the piston 48 from moving, said means being constituted in this example by a cap 50 suitable for covering the proximal end of the piston 48 and preventing the piston from being moved before the dispenser is used.

In this example, the intermediate body 14 is made up of a main portion 14a including grip means 20, and having fitted thereto a proximal endpiece 14b that carries in particular the abutment surface 21 that is visible in FIGS. 5 to 7.

Still in this example, the protective sheath 16 is provided with a main portion 16a and a proximal portion 16b that is fitted on the portion 16a. and that serves in particular to carry the retractable means 26. As in FIGS. 1 to 3, the retractable means 26 include two catches 28. The protective sheath 16 also includes a distal member 16c fitted to the main portion 16a.

The operation of the FIG. 4 device is described below with reference to FIGS. 5 to 7.

In the storage configuration shown in FIG. 5, the cap 30 for protecting the needle 24 is screwed onto the intermediate body 14, and more precisely onto the distal end of the portion 14a. thereby having the effect of moving the protective sheath 16 relative to the intermediate body 14, such that the retractable means 26 are not in contact with the abutment surface 21, and are therefore not subjected to stress by the return means 18. Furthermore, in this storage configuration, the injection device 10 is provided with the cap 50 for preventing the piston 48 from moving, thereby preventing any fraudulent or accidental movement of the piston 48 while the device 10 is in storage. More precisely, the cap 50 is mounted on the proximal end of the intermediate body 14, e.g. by snap-fastening. Since the cap 50 is relatively rigid and since it covers all of the piston 48 that projects from the proximal end of the device 10, it is not possible for the piston 48 to be moved in the device 10.

In the injection configuration, shown in FIG. 6, the cap 30 for protecting the needle and the cap 50 for preventing the piston from moving have both been removed. Because the protective cap 30 has been removed, the distal end of the sheath 16 is no longer in abutment against the cap 30. The sheath 16 is urged by the return means 18 in the direction shown by arrows 52 until the retractable means 26 come into contact with the surface 21, and thus perform their function of retaining the return means 18, retaining them under stress so as to hold the safety device in the injection configuration. In this configuration, it is possible to inject substance, and more precisely to inject the implant 46 into the body of the patient.

In this embodiment, the device 10 is an implant retro-injection device enabling the implant 46 to be injected while the needle 24 is being withdrawn from the patient's body. The means 24, 44, 48a. and 48b are implant retro-injection means. More precisely, to make an injection, the needle is initially caused to penetrate into the patient's body, and then the pusher 54 of the portion 48b of the piston 48 is pushed so as to cause the implant 46 to move out from the reception member 44 and be introduced into the inside of the hollow needle 24. Once the implant 46 is at the distal end of the hollow needle, the piston 48 is at the end of its stroke, thereby triggering automatic retro-injection of the implant 46. This retro-injection comprises a step of retracting the means 26 away from the abutment 21, this retraction being performed, for example, by a projection 56 on the portion 48b of the piston. Retraction releases the return means 18, which expand and thus thrust the protective sheath 16 downwards via the abutment surface 34. Under the effect of this thrust, the portion 16c comes into contact with the skin of the patient, such that the movement of the return means 18 causes the intermediate body 14 to move upwards until it takes up the final safe position shown in FIG. 7. During this upward movement of the intermediate body 14, the implant 46 is held at the same distance from the patient's skin as when it was at the distal end of the needle 24. The implant is held at this position by the portion 48a of the piston rod, which portion does not rise with the intermediate body 14 since it is separated from the other portion 48b secured to the intermediate body 14, as can be seen in FIG. 7. Since the needle 24 is moved upwards together with the intermediate body 14, withdrawing the needle releases a certain amount of space under the skin, which space is filled by the implant 46. At the end of this retro-injection, the device 11 is in the safe configuration.

In the safe configuration, shown in FIG. 7, the protective sheath 16 completely covers the injection needle 24, and it is held in this position by snap-fastener means provided on the sheath 16 and the intermediate body 14, and more precisely by a projection 58 from the protective sheath 16 snap-fastening in slots 60 provided in the intermediate body 14 and visible in FIG. 4.

The invention is not limited to the embodiments described above. In particular, the means for deactivating the retractable means 26 are described as being in the form of a cap 30 for protecting the needle. Nevertheless, these deactivation means could take some other form. For example, it is possible to envisage the deactivation means being provided on a part that is specific to deactivating the retractable means, or indeed on one of the other parts of the injection device 10, e.g. on the cap 50 for preventing the piston from moving.

Figure 9:
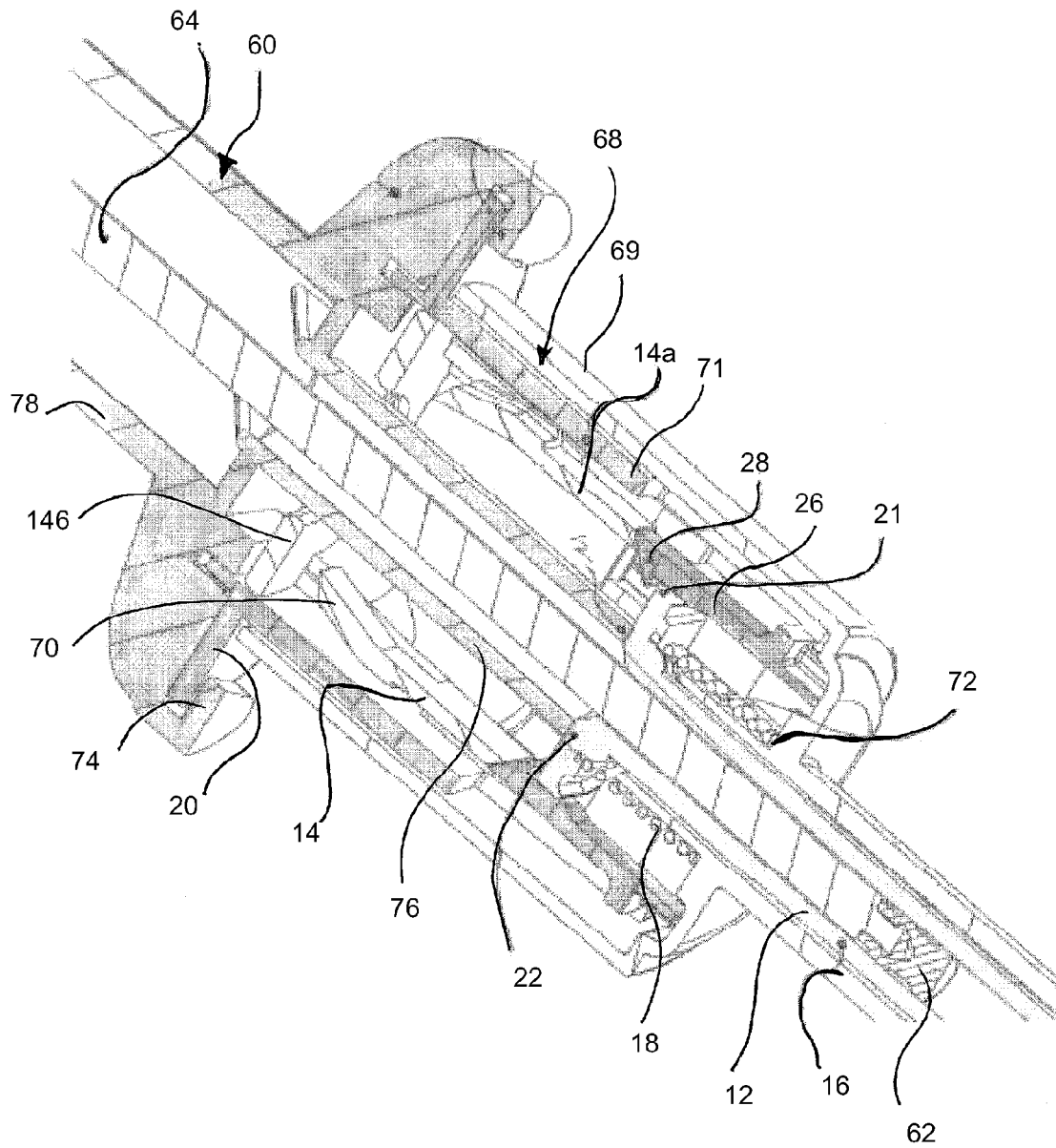
FIG. 9 is a fragmentary longitudinal section view of the FIG. 8 device in a storage configuration.

An example of a device in which the deactivation means are not carried by the cap 30 is shown in FIGS. 8 and 9, described below. Elements having functions similar to those of the embodiments of the other figures are not described again and they are given identical references.

The injection device 10 comprises the safety device 11 and the syringe 12 for injecting a liquid or a gel, the syringe being provided with a cap 30 fitted to its distal end, a piston 62, and a piston rod 64 at its proximal end. The safety device 11 comprises a protective sheath 16, an intermediate body 14, return means 18, and a storage member 60.

In this example, the sheath 16 comprises a tubular distal portion 66 and a proximal portion 68. The proximal portion 68 of the sheath comprises two fitted parts that are fastened to each other in permanent manner: namely an outer sleeve 69 extending the tube of the distal portion 66, and an internal part 71 snap-fastened in the sleeve 69. The internal part 71 carries firstly grips 20 at its proximal end, and secondly retractable retaining means 26 for retaining the return means 18, constituted in this example by two diametrically-opposite resilient tabs carrying retractable catches 28. The proximal portion 68 receives the intermediate body 14 when the device 10 is in its storage configuration or its injection configuration. In this example, the grips 20 form means for fastening the storage member 60 on the safety device 11, and ramps 65 are provided to separate the member 60 from the device, as described below.

The intermediate body 14 is substantially in the form of a cap, having side walls 14a and a top transverse wall 14b with the piston rod 64 passing therethrough. The body 14 has means 70 for snap-fastening the syringe 12 in the safe configuration, as described below.

The return means 18 comprise a compression spring bearing firstly against a seat 72 of the sheath 16, and secondly against the collar 22 of the syringe 12.

The storage member 60 is fitted to the proximal end of the device. It includes releasable fastener means 74 for fastening the member 60 on the device 11, a distal portion 76, and a proximal portion 78. The distal portion 76 is semi-tubular. It extends from the fastener means 74 towards the return means 18 and forms a spacer between the fastener means 74 and the return means 18. More precisely, in the storage configuration, the distal portion 76 bears indirectly against the return means 18 by bearing against the collar 22 on which the means 18 act so as to hold the catches 28 at a certain distance d from the abutment 21 formed on the collar 22. The fastener means 74 serve to fasten the member 60 releasably on the portion 68 of the sheath 16. In this example, they comprise slots capable of receiving the grips 20 of the portion 68. The storage member 60 also includes means for protecting the piston rod 64, which means are carried by the proximal portion 78. More precisely, the proximal portion 78 is of open semi-tubular shape, so as to receive the piston rod 64 and thus form a protective case preventing deformation of the rod and limiting access thereto.

It can be understood that the storage member 60 forms means for deactivating the retractable means 26 during storage, exerting stress on the return means 18 that is greater than the stress exerted by the retractable means 26 in the injection configuration.

The operation of the device shown in FIGS. 8 and 9 is described below.

When the device is in the storage configuration, the member 60 is fastened on the safety device 11 by co-operation between the slots 74 and the grips 20. In this configuration, the portion 76 bears against the spring 18 so as to exert stress greater than the stress exerted by the means 26 in the injection configuration. More precisely, the member 60 bears against the syringe 12 so as to avoid stressing the retractable catches 28. So long as the member 60 is in place, the means 26 are not subjected to any force from the spring 18. It should be observed that by virtue of the portion 78, the member 60 protects the piston rod 64, in particular by limiting access thereto.

In order to make an injection, the storage member 60 is removed by turning it as shown by arrow 80 so as to separate the slots 74 from the grips 20. By co-operation between the member 60 and the ramps 65, the member 60 is moved as shown by arrow 82, thereby completely disengaging it from the device 11. Once the member 60 has been separated from the device 11, the device automatically takes up its injection configuration. The spring 18 causes the collar 22 of the syringe to be pressed against the catches 28, thereby causing the collar to be retained. It is then possible to remove the cap 30 so as to uncover the needle 24 and insert it into the skin of the subject. The substance is injected by applying pressure to the proximal end 84 of the piston rod 64.

Once the dose of substance has been injected in full, the piston reaches the end of its stroke, such that the proximal end 84 of the piston rod comes into contact with the portion 14b of the intermediate body 14, thereby causing it to slide in the sheath until the walls 14a come into contact with the retractable catches 28. By continuing to press on the end 84, the catches 28 are splayed outwards by the ramp effect, such that they no longer retain the syringe 12. Thus, by releasing pressure on the end 84, the user causes the syringe 12 to move up relative to the sheath 16 under drive from the spring 18 expanding. The upward movement of the syringe has the effect firstly of causing the collar 22 to snap-fasten in the snap-fastener means 70, and secondly of causing the intermediate body to slide in the direction 82 so as to cause it to move out from the portion 68 of the device. At the end of the stroke, the intermediate body 14 is prevented from moving relative to the sheath 16 by catches formed on the intermediate body 14 snap-fastening in slots 86 formed in the proximal portion 68 of the sheath 16. In this position, the device 11 is in the safe configuration, the needle 24 being covered by the sheath 16 and thus avoiding any accidental pricking.

It will be understood that by means of the above-described safety devices, the retractable means 26 are spared while in the storage configuration, thereby guaranteeing that the retractable means 26 are not worn at the time the safety device 11 is used. Because of this protection of the retractable means 26, it is possible to make these means 26 in some other way, for example out of a material that is more flexible.

It will be understood that the above-described safety devices can be used both in an injection device having a syringe for injecting a liquid or a gel, and in an injection device serving to introduce an implant in solid or semi-liquid form.

It should be observed that the invention can have embodiments other than those described above. For example, the piston 48 of FIGS. 5, 6, and 7 is made in two portions in the example described, however it could equally well be made as a one-piece rod, which is advantageous, in particular because that reduces the number of parts to be assembled together and simplifies their shapes.

The invention claimed is:

1. A safety device for an injection device, wherein the safety device comprises:
   a protective sheath driven by a spring, the safety device being capable of taking an injection configuration in which the sheath allows an injection needle to be left uncovered, and a safe configuration in which the sheath enables the injection needle to be covered once an injection has been made;
   a retractable element for retaining the spring, the retractable element retaining the spring under stress in such a manner as to hold the safety device in the injection configuration; and
   a deactivation member for deactivating the retractable element, enabling the safety device to take a storage configuration before the injection, in which the retractable element is not subjected to stress from the spring, the member for deactivating the retractable element in the storage configuration exerting stress on the spring that is greater than the stress exerted thereon by the retractable element when in the injection configuration.

2. The device according to claim 1, wherein the deactivation member comprises a protective cap covering the needle when the device is in the storage configuration, fitting the cap on the safety device causes the retractable element to be deactivated.

3. The device according to claim 1, wherein the retractable element for retaining the spring comprise retractable catches, the catches being in abutment against a surface when the device is in the injection configuration and being retracted from said abutment when the device is in the safe configuration; the deactivation member holding the catches at a certain distance from the abutment when the device is in the storage configuration.

4. The device according to claim 1, wherein the deactivation member comprises a storage member mounted on the proximal end of the device and bearing directly or indirectly against the spring to cause it to take up its storage configuration.

5. The device according to claim 4, the storage member comprising a removable fastener on the device and a distal portion extending from the fastener and forming a spacer between the fastener and the spring.

6. The device according to claim 4, wherein the storage member includes protection for a piston rod.

7. An injection device, including a safety device according to claim 1.

8. The device according to claim 1, the device being a device for injecting an implant and including an implant retro-injector.

9. The device according to claim 7, the device being a device for injecting a liquid or a gel and comprising a liquid injection syringe.

10. A method of assembling an injection device including a safety device according to claim 1, the method comprising the steps of:
slidably mounting the sheath relative to an intermediate body;
retaining the spring firstly against the sheath and secondly against the intermediate body; and
fitting a piston rod or a syringe to the injection device once the safety device is in the storage configuration.

11. A safety device for an injection device, wherein the safety device comprises:
a protective sheath driven by a spring, the safety device being capable of taking an injection configuration in which the sheath allows an injection needle to be left uncovered, and a safe configuration in which the sheath enables the injection needle to be covered once an injection has been made;
a retractable element for retaining the spring, the retractable element retaining the spring under stress in such a manner as to hold the safety device in the injection configuration; and
a deactivation member for deactivating the retractable element, enabling the safety device to take a storage configuration before the injection, in which the retractable element is not subjected to stress from the spring, the member for deactivating the retractable element in the storage configuration exerting stress on the spring that is greater than the stress exerted thereon by the retractable element when in the injection configuration;
wherein the deactivation member comprises a protective cap covering the needle when the device is in the storage configuration, fitting the cap on the safety device causes the retractable element to be deactivated by moving the protective sheath.

* * * * *